(12) United States Patent
Yagi

(10) Patent No.: US 6,753,955 B2
(45) Date of Patent: Jun. 22, 2004

(54) INSPECTION DEVICE FOR CRYSTAL DEFECT OF SILICON WAFER AND METHOD FOR DETECTING CRYSTAL DEFECT OF THE SAME

(75) Inventor: Shinichiro Yagi, Gunma (JP)

(73) Assignee: Shin-Etsu Handotai Co., Ltd., Tokyo (JP)

( * ) Notice: Subject to any disclaimer, the term of this patent is extended or adjusted under 35 U.S.C. 154(b) by 183 days.

(21) Appl. No.: 09/914,044

(22) PCT Filed: Dec. 22, 2000

(86) PCT No.: PCT/JP00/09135
§ 371 (c)(1),
(2), (4) Date: Dec. 11, 2001

(87) PCT Pub. No.: WO01/48810
PCT Pub. Date: Jul. 5, 2001

(65) Prior Publication Data
US 2002/0167661 A1 Nov. 14, 2002

(30) Foreign Application Priority Data
Dec. 24, 1999 (JP) ............................................ 11-365947

(51) Int. Cl.[7] ............................................... G01N 21/00
(52) U.S. Cl. ................................ 356/237.3; 356/237.1; 356/237.2; 356/237.4
(58) Field of Search .......................... 356/237.1, 237.2, 356/237.3, 237.4, 237.5

(56) References Cited

U.S. PATENT DOCUMENTS

| | | | | |
|---|---|---|---|---|
| 6,143,629 A | * | 11/2000 | Sato | 438/455 |
| 6,146,911 A | * | 11/2000 | Tsuchiya et al. | 438/14 |
| 6,171,982 B1 | * | 1/2001 | Sato | 438/795 |
| 6,239,045 B1 | * | 5/2001 | Tanaka et al. | 1/1 |
| 6,413,874 B1 | * | 7/2002 | Sato | 438/714 |
| 6,506,665 B1 | * | 1/2003 | Sato | 438/458 |
| 2001/0014544 A1 | * | 8/2001 | Tanaka et al. | 438/905 |

FOREIGN PATENT DOCUMENTS

| | | |
|---|---|---|
| EP | 796933 | 9/1997 |
| JP | 11-100299 | 4/1999 |
| JP | 11-237225 A | 8/1999 |
| JP | 2000-228364 | 8/2000 |

* cited by examiner

*Primary Examiner*—Rodney Fuller
(74) *Attorney, Agent, or Firm*—Crowell & Moring LLP

(57) ABSTRACT

An inspection object silicon wafer for the purpose of detecting crystal defects and the method of detection thereof, which make easy the detection of the number and location of the defects formed on the surface of the silicon wafer by performing heat treatment and epitaxial growth under a temperature condition in which the natural oxide film is removed but the state of the surface of the silicon wafer is preserved, specifically under a hydrogen atmosphere of normal pressure and a temperature between 900° C. and 1080° C., through which defects having pits and projections are generated on the surface of the epitaxial layer, and by detecting the defects having pits and protrusions by a light scattering type particle inspection apparatus.

5 Claims, 3 Drawing Sheets

INSPECTION DEVICE FOR CRYSTAL DEFECT OF SILICON WAFER AND METHOD FOR DETECTING CRYSTAL DEFECT OF THE SAME

FIELD OF THE INVENTION

The present invention relates to a silicon wafer for the purpose of detecting crystal defects and the method of detection thereof, specifically to a silicon wafer for the purpose of detecting crystal defects and the method of detection thereof, in which crystal defects formed on the surface of the silicon wafer are shown up in pits and projections by forming epitaxial layer.

TECHNICAL BACKGROUND

A silicon wafer is the general term for a silicon single crystal subtrate (hereafter may be referred to as "mirror surface wafer") made by slicing the single crystal grown by Czochralski method (CZ method) or Floating zone melting method (FZ method) to thin plate and further polishing the surface to a mirror surface state (hereafter may be referred to as "mirror surface wafer") or a silicon epitaxial wafer obtained by forming a thin film of silicon single crystal on the mirror surface wafer by vapor phase growth. A variety of crystal defects such as point defect, line defect, plane defect, etc. are formed in a silicon wafer. Among these, the one appearing on the surface (hereafter may be referred to as "surface defect") exerts an influence to the electric characteristic of semiconductor devices having circuits formed in near proximity to the surface of the silicon wafer, and the adequate control of the condition of detect generation is needed.

As the surface detect has ordinarily no virtual pit or projection, it is shown up in pit or projection by preferential etching to be detected. Sirtl solution, Secco solution, and Wright solution are well known as solutions for preferential etching. For example, Secco solution is a aqueous solution of 28.86 mol of 50% hydrofluoric acid and 0.15 mol of potassium bichromate ($K_2Cr_2O_7$). These are etching solutions which oxidize silicon with the oxidizing agent and solve the oxide film with hydrofluoric acid. Crystal defects are made apparent by producing pits and/or projections through a phenomenon that the speed of oxidation by the oxidizing agent differs between oxidation of perfect crystal and that of a region where crystal defects or stresses exist.

Surface defects made apparent by the preferential etching are observed by a normalski type differential interference microscope to determine its density. The normalski type differential interference microscope gives a three-dimensional appearance of irregularity and ruggedness of height of 3.5 nm or higher, and the inclination of plane is observed as a difference in interference color.

The density of surface defects is determined by observing 5 to 9 points of area or scanning in the direction of diameter by 100× to 400× magnification. The number of defects per silicon wafer is worked out from the detected number of defects and the measurement area.

For example, when a silicon wafer of 200 mm diameter is scanned in the direction of diameter in the shape of a cross by the differential interference microscope, if the diameter of the field of view of the microscope is 1.7 mm, then the measurement area is:

$$1.7 \text{ mm} \times 200 \text{ mm} \times 2 = 680 \text{ mm}^2.$$

Supposing that one surface defect is observed by the scanning, the number of surface defects per silicon wafer is:

$$1(\text{defect}) \times (\pi \times 100^2 \text{ mm}^2) \div 680 \text{ mm}^2 \fallingdotseq 46(\text{defect}).$$

The above value 46 of the number of surface defects per silicon wafer is effective only when the surface defects are distributed evenly. When the surface defects appear localized in a region, the above value differs far from the real state. Also, when the density of surface defects is small, for example, when the number of surface defects per silicon wafer of diameter of 200 mm is under 46, there is high probability that no surface defect exists in the region scanned by the microscope and detection is substantially impossible.

Further, in the case of a silicon wafer of resistivity of 0.02 Ωcm or smaller, surface defects are difficult to appear by etching with aforesaid preferential etching solutuon.

On the other hand, there is visual inspection using collimated light as a method of simply inspecting the whole surface of a silicon wafer.

In the visual inspection, when the surface of a preferentially-etched silicon wafer is irradicated by collimated light, scattered light is reflected from surface defects. The distribution pattern of the surface defects is observed by viewing the scattered light in a darkroom. But, by this visual inspection, mapping of the surface defects on the whole surface can not be obtained by using a machine, and the accurate determination of the number and location of surface defects is not possible.

Also, when trying to detect the surface defects appearing on the surface of the silicon wafer by preferential etching by means of the light scattering type particle inspection apparatus, the etched figures generated by the preferential etching are detected similarly as particles together with the surface defects, and the surface defects can not be discriminated from the etched figures.

SUMMARY OF THE INVENTION

The present invention was made to solve the aforementioned problem. Accordingly, the object of the invention is to provide a silicon wafer on the surface of which the number and location of crystal defects generated can be easily detected and the method of detection thereof.

Usually, before performing epitaxial growth, heat treatment is performed in a hydrogen atmosphere at normal pressure and a temperature between 1100° C. and 1200° C. for etching the natural oxide film formed on the surface of a silicon wafer and for etching the silicon surface for the purpose of eliminating the crystal defects generated on the surface of the silicon wafer. The etching of the natural oxide film and that of the silicon surface are instantly completed at the above-mentioned temperature range. Then, by vapor phase growth of silicon single crystal thin film on the surface of the cleaned silicon wafer, an epitaxial layer with largely reduced surface defects is formed.

The etching of the natural oxide film by hydrogen can be effected at temperatures above 900° C. at normal pressure, but, on the other hand, the speed of etching a silicon surface by hydrogen decreases rapidly when the temperature of heat treatment is lower than 1100° C. and the etching hardly occurs below 1080° C.

Therefore, if a silicon wafer is heat-treated at a temperature between 900° C. and 1080° C. in a hydrogen atmosphere of normal pressure, the natural oxide film is completely removed but the surface of the silicon wafer is hardly etched, thus the surface condition is preserved and also the surface defects are preserved without being removed.

After this heat treatment, if a silicon single crystal film is grown in vapor phase on the silicon wafer at a temperature between 900° C. and 1080° C. at normal pressure, the surface defects are preserved during the vapor phase growth and transferred to the epitaxial layer. Thus, the surface defects on the silicon wafer become apparent on the surface of the epitaxial layer as crystal defects having pits and/or projections.

As the crystal defects appearing on the surface of the epitaxial layer have pits and/or projections, they are detected by a light scattering type particle inspection apparatus like particles are detected.

The present invention was made based on the above mentioned findings. The inspection object silicon wafer for the purpose of detecting crystal defects is characterized in that epitaxial growth is made on the surface of a mirror surface wafer which the natural oxide film is removed of without surface defects being eliminated to make the crystal defects having pits and/or projections appear on the surface of the epitaxial layer.

The inspection object silicon wafer for the purpose of detecting crystal defects is manufactured through a process of heat treatment in which the natural oxide film is removed without the surface defects of a mirror surface wafer being eliminated, and a process of epitaxial growth in which the epitaxial growth is made on the surface of the mirror surface wafer and the crystal defects having pits and/or projection are generated on the surface of the epitaxial layer.

More concretely, the heat treatment process and epitaxial growth process are preferably performed under a hydrogen atmosphere of normal pressure at a temperature between 900° C. and 1080° C.

The crystal defect detection method according to the present invention relates to a detection method which can easily detect the number and location of the crystal defects formed on the surface of a silicon wafer by use of said inspection object. The method is characterized in that; by making epitaxial growth on the surface of a silicon wafer heat-treated under a temperature condition in which the natural oxide film is removed but the surface state of the silicon wafer is preserved, crystal defects having pits and projections are made to appear on the surface of the epitaxial layer; and the crystal defects having pits and projections are detected by a light scattering particle inspection apparatus. Further preferably the heat treatment and the growth of epitaxial layer are performed under a hydrogen atmosphere of ordinary atmosphere at a temperature between 900° C. and 1080° C.

BEST MODE FOR CARRYING OUT THE INVENTION

A preferred embodiment of the present invention will now be detailed with reference to the accompanying drawings. It is intended, however, that unless particularly specified, dimensions, materials, relative positions and so forth of the constituent parts in the embodiments shall be interpreted as illustrative only not as limitative of the scope of the present invention.

EXAMPLE

Figure 3A:
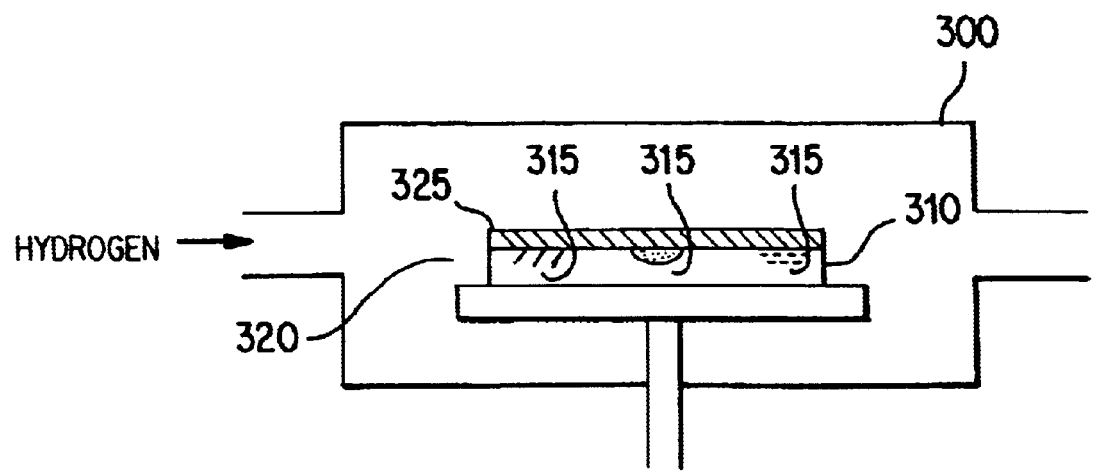
FIG. 3(a) is a drawing illustrating the surface condition of a silicon wafer before epitaxial growth.
Figure 3B:
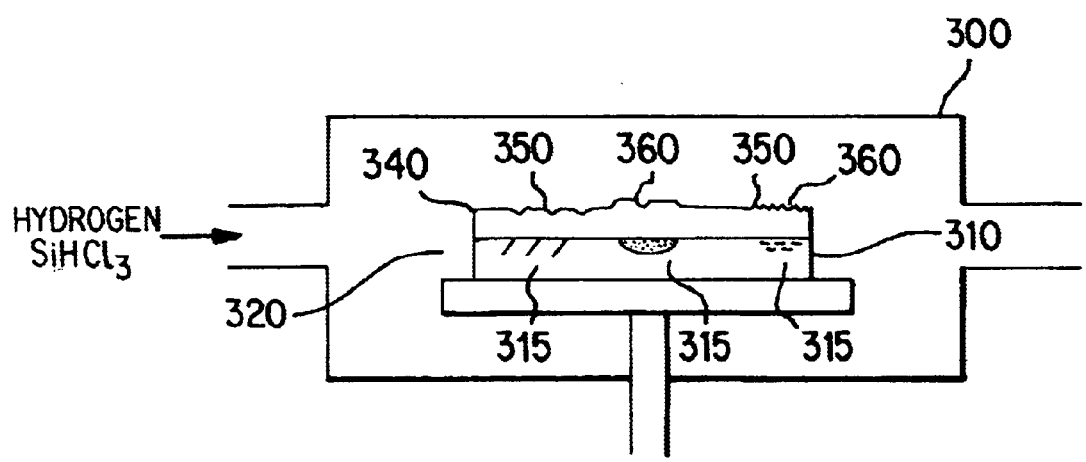
FIG. 3(b) is a drawing illustrating the surface condition of a silicon wafer after epitaxial growth.

Nine p type silicon single crystal rods having a diameter of 200 mm and a resistivity of 0.01 Ωcm ~0.02 Ωcm were prepared, each rod having a different crystal defect density by varying the pulling-condition of the single crystal and/or the inside structure of the furnace. Then, the silicon single crystal rods were sliced to thin plates, and the surfaces of the sliced plates were mirror polished to obtain mirror surface wafers 310 of plane orientation of (100). (See FIGS. 3a and 3b.) The mirror surface wafers 310 obtained from each silicon single crystal rod were separated into two groups, one for preferential etching and another for vapor phase growth.

The mirror surface wafers 310 for preferential etching were etched by said Secco solution, and surface defects 315 appearing as etch pits by the preferential etching were observed by means of a Normaiski type differential interference microscope.

The observation by the microscope was done by scanning the main surface of the preferentially etched mirror surface wafers by 100× magnification in the direction of diameter in the shape of a cross, and the number of etch pits per wafer was calculated from the number of etch pits observed and the measurement area.

Figure 4:
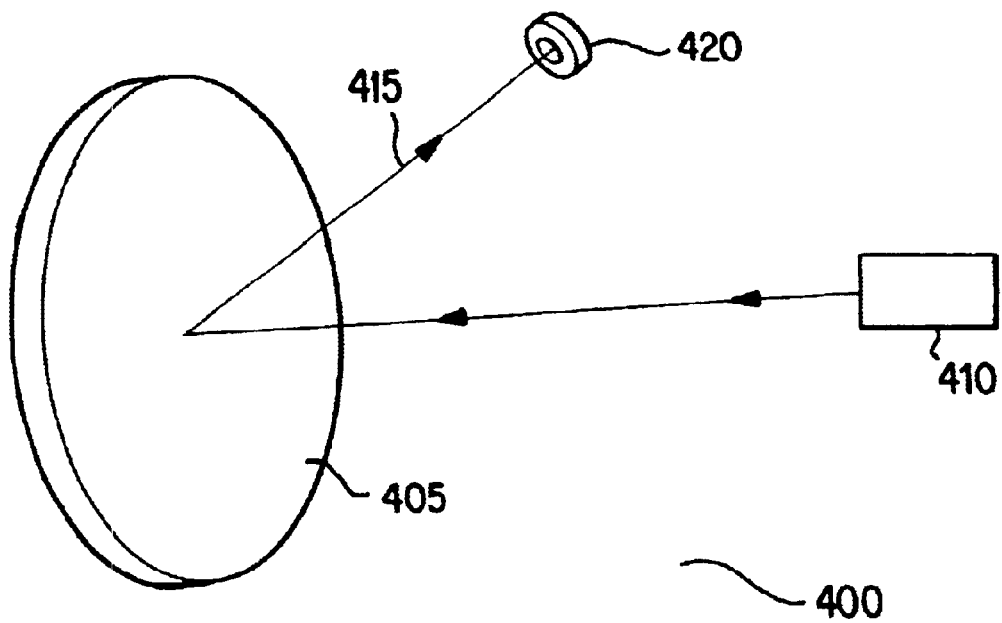
FIG. 4 is a schematic illustration of a light scattering type particle inspection apparatus.

On the other hand, the mirror surface wafers 310 for vapor phase growth were placed in a vapor phase growth furnace 300 held to a hydrogen atmosphere 320. After three minutes of heat treatment at normal pressure and a temperature of 1050° C. which results in removal of the natural oxide film 325 while hardly etching the surface of the silicon wafer, trichlorosilane_($SiHCl_3$) gas was supplied while keeping the temperature of 1050° C. to allow an epitaxial layer 340 of 4 μm thick and resistivity of 5 Ωcm to grow at normal pressure. Thus treated wafers were prepared as inspection object silicon wafers (405 in FIG. 4). When said inspection object silicon wafers 405 for the purpose of detecting crystal defects, which are mirror surface wafers 310 with epitaxial layer 340 formed on the surface, were measured by a light scattering type particle inspection apparatus 400, crystal defects such as stacking faults$_{13}$(SF) and dislocation defects having pits 350 and/or projections 360 were apparent on the surface of said inspection objects and detected as particles by detecting scattered light 415 generated by light source 410 with detector 420.

When said inspection object silicon wafers 405 for the purpose of detecting crystal defects, which are mirror surface wafers 310 with epitaxial layer 340 formed on the surface, were measured by a light scattering type particle inspection apparatus 400, crystal defects such as stacking faults$_{13}$(SF) and dislocation defects having pits 350 and/or projections 360 were apparent on the surface of said inspection objects and detected as particles by detecting scattered light 415 generated by light source 410 with detector 420.

In the example, particles equal to or larger than 0.1 μm in diameter were detected over the whole surface of the inspection object wafers excluding the peripheral part of 5 mm from the outer edge of each wafer.

Figure 1:
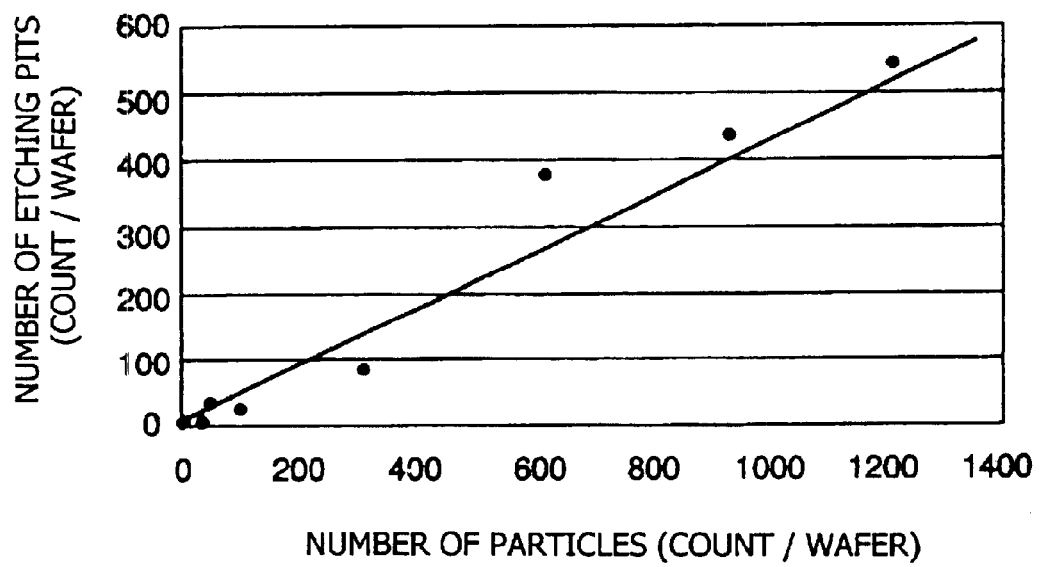
FIG. 1 is a graph showing the correlation between the number of etch pits and that of particles corresponding to that of crystal defects on epitaxial layer surface.

FIG. 1 shows a correlation between the number of particles on the surface of the epitaxial layer and that of etch pits measured by the light scattering type particle inspection apparatus in the example.

From FIG. 1, it is recognized that there is a good correlation between the number of particles and that of etch pits.

Figure 2:
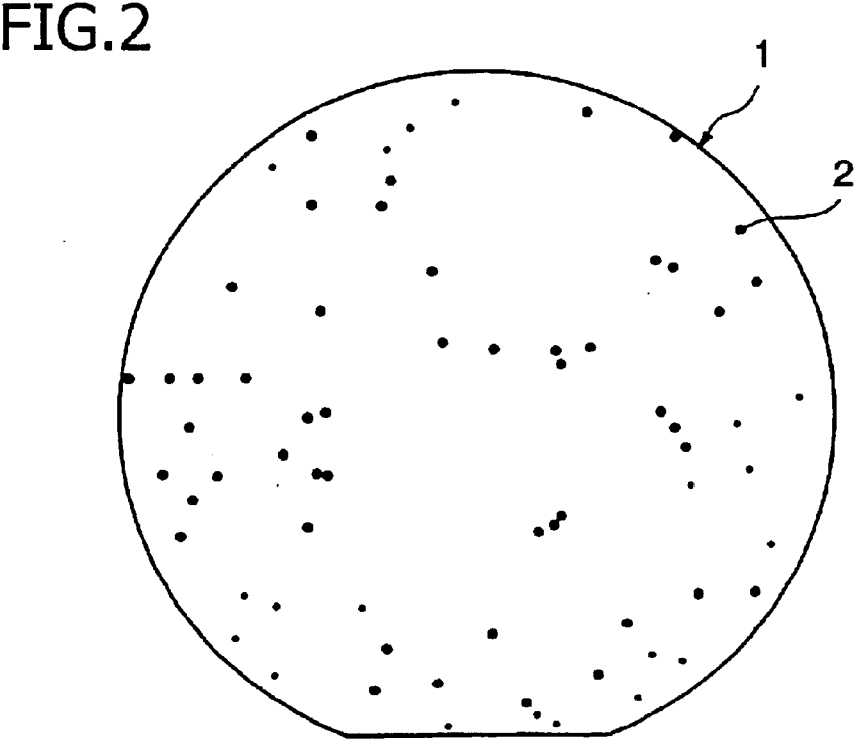
FIG. 2 is a map showing the distribution of the crystal defects formed on the surface of a silicon wafer. In the drawings, reference number 1 denotes an inspection object for the purpose of determining crystal defects, reference number 2 denotes crystal defects.

FIG. 2 shows an example of measurement of crystal defects 2 appearing on the surface of the inspection object wafer 1 manufactured according to the aforementioned procedure.

From FIG. 2, it is recognized that the number and location of the crystal defects formed on the surface of the mirror surface wafer are easily determined, for the crystal defects 2 appearing on the surface of the epitaxial layer grown under the condition mentioned above can be output in a map state all over the surface of the wafer 1 through detection by the light scattering type particle inspection apparatus like conventional particles have been detected.

Further, although in the example it was shown that the number and location of crystal defects formed on the mirror Surface wafer was able to be detected by a light scattering type particle inspection apparatus, but also the identification of the kind of defect is possible by thinning the crystal defect part by use of a Focused Ion Beam apparatus based on the detected information on the defects and observing the part by a transmission electron microscope.

Still further, the present invention is adaptable not only to wafers having defects caused by crystal growth but to wafers having defects caused by machining in the process of manufacturing mirror surface wafers.

For example, discrimination of defects caused by crystal growth from those caused by machining is possible in the way in which defects on the surface of an inspection object wafer according to the present invention are detected, then the epitaxial layer on the surface of the inspection object wafer is removed by mirror polishing or by non-selective etching by use of mixed acid of hydrofluoric acid and nitric acid, etc. to get a mirror surface, and after an epitaxial layer is grown again by the method according to the present invention, defects are detected by a light scattering type particle inspection apparatus.

Although, in the example, measurement object wafers were mirror surface wafers, silicon wafers other than the mirror surface wafers are adaptable, for example, an epitaxial wafer of which the surface is again mirror polished and which having virtually no pits and projections, as far as pits and projections are generated by epitaxial growth.

INDUSTRIAL APPLICABILITY

As cited above, by use of the inspection object silicon wafer and method of detection of surface defects according to the present invention, the number and location of the surface defects formed on the surface of the silicon wafer can be detected.

What is claimed is:

1. An inspection object silicon wafer for the purpose of detecting crystal defects characterized in that epitaxial growth is made on a surface of a mirror surface wafer from which a natural oxide film is removed without surface defects being eliminated to make the crystal defects having pits and projections appear on a surface of an epitaxial layer.

2. An inspection object silicon wafer for the purpose of detecting crystal defects manufactured through a process of heat treatment in which a natural oxide film is removed without eliminating surface defects of a mirror surface wafer and a process of epitaxial growth in which epitaxial growth is made on a surface of the mirror surface wafer and the crystal defects are generated as defects having pits and projections on a surface of the epitaxial layer.

3. An inspection object silicon wafer for the purpose of detecting crystal defects according to claim 2, wherein the heat treatment process and epitaxial growth process are performed under a hydrogen atmosphere of normal pressure at a temperature between 900° C. and 1080° C.

4. A method of detecting crystal defects of a silicon wafer characterized by:

making epitaxial growth on the surface of the silicon wafer heat-treated in a temperature condition in which the natural oxide film is removed but the surface state of the silicon wafer is preserved, wherein crystal defects having pits and projections are made to appear on the surface of an epitaxial layer; and detecting the crystal defects having pits and projections by a light scattering particle inspection apparatus.

5. A method of detecting crystal defects of a silicon wafer according to claim 4, wherein the heat treatment and the growth of epitaxial layer are performed under a hydrogen atmosphere of normal pressure at a temperature between 900° C. and 1080 ° C.

* * * * *